(12) United States Patent
Muto

(10) Patent No.: US 8,992,015 B2
(45) Date of Patent: Mar. 31, 2015

(54) OPHTHALMOLOGIC APPARATUS AND CONTROL METHOD THEREOF

(75) Inventor: Kenji Muto, Fujisawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 385 days.

(21) Appl. No.: 13/634,509

(22) PCT Filed: Mar. 24, 2011

(86) PCT No.: PCT/JP2011/058160
§ 371 (c)(1),
(2), (4) Date: Sep. 12, 2012

(87) PCT Pub. No.: WO2011/122684
PCT Pub. Date: Oct. 6, 2011

(65) Prior Publication Data
US 2013/0003017 A1    Jan. 3, 2013

(30) Foreign Application Priority Data

Mar. 31, 2010    (JP) .................................. 2010-082805

(51) Int. Cl.
*A61B 3/14* (2006.01)
*A61B 3/00* (2006.01)
*A61B 3/10* (2006.01)

(52) U.S. Cl.
CPC ..................................... *A61B 3/102* (2013.01)
USPC ............ 351/206; 351/200; 351/210; 351/221

(58) Field of Classification Search
USPC ......... 351/206, 200, 205, 209, 210, 221–223, 351/246
See application file for complete search history.

(56) References Cited

U.S. PATENT DOCUMENTS

2011/0102742 A1*    5/2011    Miyasa et al. ................ 351/206

FOREIGN PATENT DOCUMENTS

| JP | 2005511233 A | 4/2005 |
|---|---|---|
| JP | 2008508068 A | 3/2008 |
| JP | 2008203246 A | 9/2008 |
| JP | 2010012166 A | 1/2010 |
| JP | 2010220774 A | 10/2010 |
| WO | 2008116270 A1 | 10/2008 |

* cited by examiner

*Primary Examiner* — Dawayne A Pinkney
(74) *Attorney, Agent, or Firm* — Canon USA Inc. IP Division

(57) ABSTRACT

An ophthalmologic apparatus includes a scanning optical system configured to scan a plurality of different regions of a test eye with a plurality of different measurement light beams, an acquisition unit configured to acquire information about a shape of the test eye, and an adjustment unit configured to adjust a relative position between an output end of a measurement light beam that serves as a reference among the plurality of measurement light beams and an output end of other measurement light beams among the measurement light beams based on the acquired information about the shape of the test eye.

7 Claims, 10 Drawing Sheets

OPHTHALMOLOGIC APPARATUS AND CONTROL METHOD THEREOF

TECHNICAL FIELD

The present invention relates to an ophthalmologic apparatus and a control method thereof, and in particular, to position adjustment of a plurality of measurement light beams.

BACKGROUND ART

Recently, an ophthalmologic apparatus using optical coherence tomography (OCT) (hereinafter, sometimes referred to as "OCT apparatus") that utilizes interference produced by low coherence light are being developed for practical use.

An OCT apparatus can obtain a high resolution tomographic image by irradiating measurement light on a sample and causing the backward scattering light from the sample (returning light) to interfere with reference light. Since the OCT apparatuses can acquire a tomographic image of a retina in a fundus of a test eye and an anterior eye, the OCT apparatuses are widely utilized to perform ophthalmologic diagnosis of the retina, cornea, and the like.

For example, for measurement performed by OCT in ophthalmologic diagnosis of the retina, there is a risk of positional deviation or missing in the tomographic image occurring due to movement of the eyeball, as represented by involuntary eye movement during visual-fixation. Especially, when measurement is performed at a wide angle of view, since it takes time to acquire the tomographic image, there is an increased chance of this risk occurring.

Accordingly, to shorten the measurement time, Japanese Unexamined Patent Application Publication (Translation of PCT Application) No. 2008-508068 discusses a method that uses a plurality of measurement light beams (hereinafter, sometimes simply referred to as "beams") to narrow the measurement region per beam. According to Japanese Unexamined Patent Application Publication No. 2008-508068, an interferometer splits the plurality of beams respectively into measurement light beams and reference light beams. The interference light produced by each of the beams is dispersed, and the dispersed interference light is detected by a two-dimensional sensor array that is the same for all of the plurality of beams.

However, with the technique discussed in Japanese Unexamined Patent Application Publication No. 2008-508068, the position of the plurality of measurement light beams with respect to the structure of the test eye cannot be adjusted.

Further, when imaging of the test eye is performed at an especially wide angle of view with a plurality of beams, depending on the test eye, focal position deviation can occur between the center and the periphery. For example, when an image plane of the measurement light is determined so that scanning is performed based on a test eye that has a normal refractive power, focal position deviation can occur for a myopic test eye.

CITATION LIST

Patent Literature

PTL 1 Japanese Unexamined Patent Application Publication (Translation of PCT Application) No. 2008-508068

SUMMARY OF INVENTION

The present invention is directed to improving quality of an image acquired based on a plurality of measurement light beams by adjusting a focal position of each measurement light beam.

According to an aspect of the present invention, an ophthalmologic apparatus includes a scanning optical system configured to scan a plurality of different regions of a test eye with a plurality of different measurement light beams, an acquisition unit configured to acquire information about a shape of the test eye, and an adjustment unit configured to adjust a relative position between an output end of a measurement light beam that serves as a reference among the plurality of measurement light beams and an output end of other measurement light beams among the measurement light beams based on the acquired information about the shape of the test eye.

Further features and aspects of the present invention will become apparent from the following detailed description of exemplary embodiments with reference to the attached drawings.

BRIEF DESCRIPTION OF DRAWINGS

The accompanying drawings, which are incorporated in and constitute a part of the specification, illustrate exemplary embodiments, features, and aspects of the invention and, together with the description, serve to explain the principles of the invention.

DESCRIPTION OF EMBODIMENTS

Various exemplary embodiments, features, and aspects of the invention will be described in detail below with reference to the drawings.

In a first exemplary embodiment, an ophthalmologic apparatus (OCT apparatus) in which the present invention is applied will be described with reference to FIG. 1.

Figure 1:
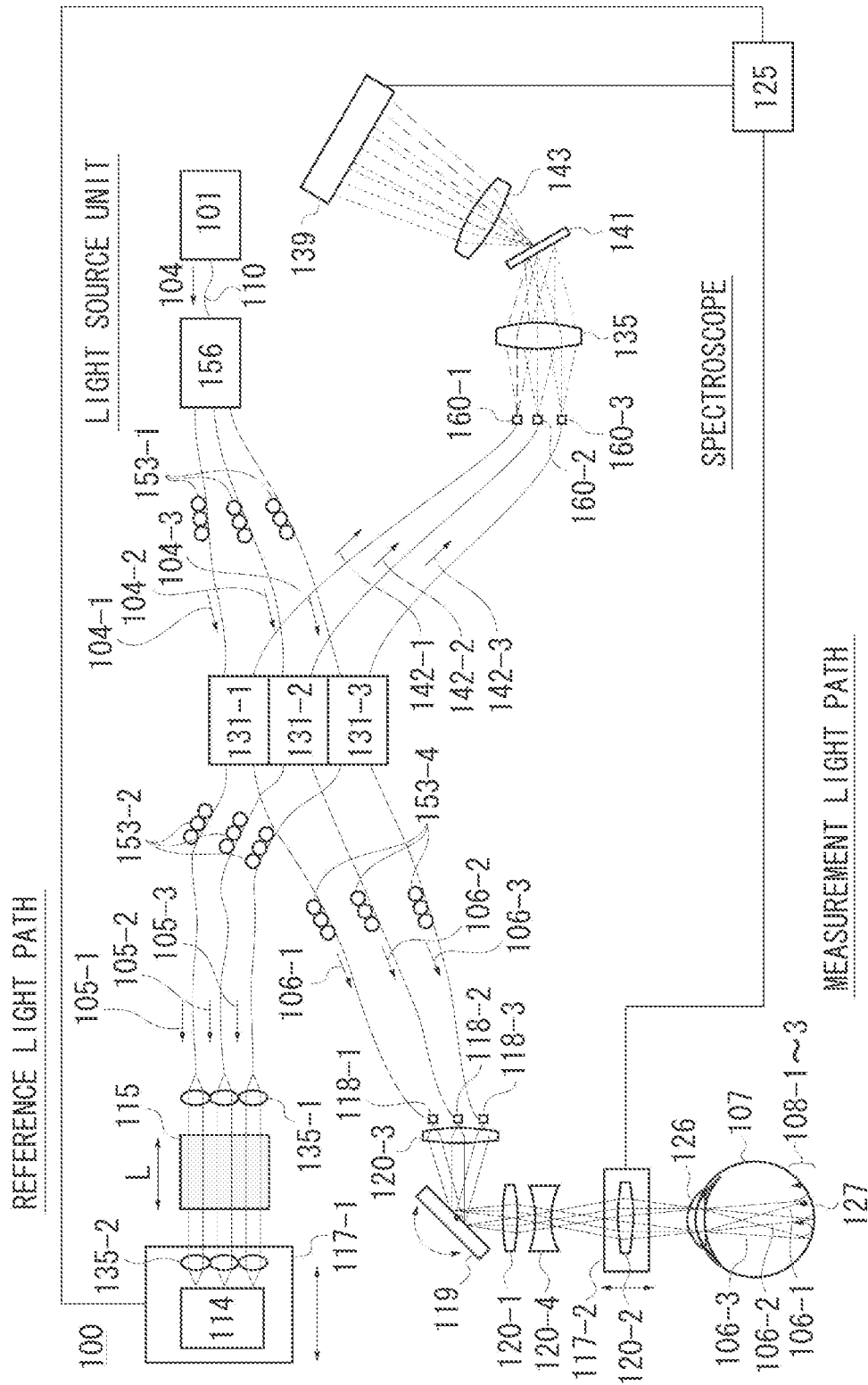
FIG. 1 is a schematic diagram illustrating a configuration of an ophthalmologic apparatus according to an exemplary embodiment of the present invention.

As illustrated in FIG. 1, an OCT apparatus 100 according to the present exemplary embodiment is formed overall as a Michelson interferometer. Each of the below-described constituent elements is operated under the control of a control unit (central processing unit (CPU)) 125. First, light output from a light source is split into measurement light and reference light. Then, a plurality of measurement light beams is irradiated via a respective measurement light path on an object to be inspected (inspection object). Using a plurality of multiplexed light beams in which returning light produced by the plurality of measurement light beams and a plurality of reference light beams that passed along a reference light path are multiplexed to produce optical interference, a tomographic image of the inspection object is imaged.

More specifically, in FIG. 1, output light 104, which is light output from a light source 101, is guided to a single mode fiber 110, and is incident on an optical coupler 156. The light is then split by the optical coupler 156 into output light beams 104-1 to 104-3, which pass along three light paths, a first light path, a second light path, and a third light path, respectively.

Further, each of these three output light beams 104-1 to 104-3 passes through a polarized light controller 153-1, and is split into reference light beams 105-1 to 105-3 and measurement light beams 106-1 to 106-3 by optical couplers 131-1 to 131-3.

The thus-split three measurement light beams 106-1 to 106-3 are reflected or scattered by a fundus 127 in a test eye 107, which is an observation target, and returned as returning light beams 108-1 to 108-3. Then, the light beams 108-1 to 108-3 are multiplexed with the reference light beams 105-1 to 105-3, which have passed along the reference light paths, by the optical couplers 131-1 to 131-3 to form synthesized light beams 142-1 to 142-3.

The light source 101 vicinity will now be described. The light source 101 is a super luminescent diode (SLD) which is a representative low-coherence light source. The light source 101 has a center wavelength of 840 nm and a band width of 50 nm. The band width is an important parameter, as it influences the resolution in an optical axis direction of the obtained tomographic image. Further, although a SLD is selected here, other types of light source may be employed as the light source 101. For example, as long as low-coherence light can be output, amplified spontaneous emission (ASE) may be used.

Considering that a fundus is to be measured, infrared light is suitable as the wavelength. In addition, since the center wavelength influences the resolution in the horizontal direction of the obtained tomographic image, it is desired that the wavelength is as short as possible. In the present exemplary embodiment, the wavelength is 840 nm. Depending on a measurement site of the observation target, some other wavelength may be selected.

Next, the light paths of the reference light 105 will be described. The reference light beams 105-1 to 105-3 pass through a polarized light controller 153-2, are converted into roughly parallel light by a lens 135-1, and output. Then, the reference light beams 105-1 to 105-3 pass through a dispersion compensating glass 115, and are concentrated on a mirror 114 by a lens 135-2. Next, the reference light beams 105-1 to 105-3 are reflected by the mirror 114, and again head toward the optical couplers 131-1 to 131-3.

The dispersion compensating glass 115 compensates the reference light 105 for the dispersion that occurred when the measurement light 106 made a round trip to the test eye 107 and a scanning optical system. In the present exemplary embodiment, as a representative value of an average eyeball diameter for a Japanese person, a value L=23 mm will be used. An electric stage 117-1 can move in the direction indicated by the arrow in FIG. 1, so that a light path length of the reference light 105 can be adjusted and controlled.

The electric stage 117-1 can be controlled by the control unit (CPU) 125. In the present exemplary embodiment, although the same mirror 114, electric stage 117-1, and dispersion compensating glass 115 are used for all three lights paths, these units may be independently configured. In such a case, so that the respective light path lengths for the reference light beams 105-1 to 105-3 can be changed, the lens 135-2 and the mirror 114 include a different electric stage 117-1, and their position is controlled for each reference light beam.

Next, the light paths of the measurement light 106 will be described. The measurement light beams 106-1 to 106-3 pass through a polarized light controller 153-4, are output from respective fiber ends 118-1 to 118-3, which are output ends of the measurement light, are converted into roughly parallel light by a lens 120-3, and are then incident on a mirror of an XY scanner 119 that forms the scanning optical system. Although, for convenience, the XY scanner 119 is illustrated here as having one mirror, in actual fact the XY scanner 119 may be configured from two mirrors, an X scanning mirror and a Y scanning mirror that are arranged near to each other, for performing raster scanning of the fundus 127 in a perpendicular direction to the optical axis.

Lenses 120-1, 120-3, and 120-4 are adjusted so that the center of each of the measurement light beams 106-1 to 106-3 generally matches the rotational center of the XY scanner mirror. In addition, a beam expander which is configured from the lenses 120-1 and 120-4 enables the beam diameter of the measurement light beams 106-1 to 106-3 to be varied. The lenses 120-1, 120-2, and 120-4 form an optical system for scanning the fundus 127. The measurement light 106 has a role of scanning the fundus 127 using vicinity of an iris 126 as a fulcrum. A scan image can be obtained at each position on the fundus 127 by driving the XY scanner 119.

An electric stage 117-2 can move in the direction indicated by the arrow in FIG. 1, so that a position of the accompanying lens 120-2 can be adjusted and controlled. By adjusting the position of the lens 120-2, a plurality of focal positions with respect to the fundus 127 of the measurement light beams 106-1 to 106-3 can be simultaneously adjusted. Although the apparatus also can perform individual adjustment, that will be described below. The electric stage 117-2 can be controlled by the control unit (CPU) 125.

In the present exemplary embodiment, although the fiber ends 118-1 to 118-3 are arranged in roughly the same plane (XZ plane), the present invention is not limited to this arrangement. For example, the fiber ends 118-1 to 118-3 may be arranged in a perpendicular direction to the paper surface (y direction), or have a component in both directions. By configuring in the above manner, the three beams can be used for scanning simultaneously.

Next, the configuration of a spectroscope in the OCT apparatus of the present exemplary embodiment will be described. The above described synthesized light 142 is output from fiber ends 160-1 to 160-3, and converted into roughly parallel light by a lens 135. The roughly parallel light is incident to a transmissive diffraction lattice 141 that forms a detection unit, and is dispersed into light of different wavelengths. The dispersed light is concentrated by an imaging lens 143, and the intensity of the light is converted into a voltage for each position (wavelength) by a line sensor. Consequently, three interference fringes of spectral regions on the wavelength axis are observed on a line sensor 139.

Acquisition of a tomographic image using the OCT apparatus will now be described. Here, acquisition of a tomographic image of the fundus 127 (parallel plane to the optical axis) will be described with reference to FIGS. 2A to 2D.

Figure 2A:
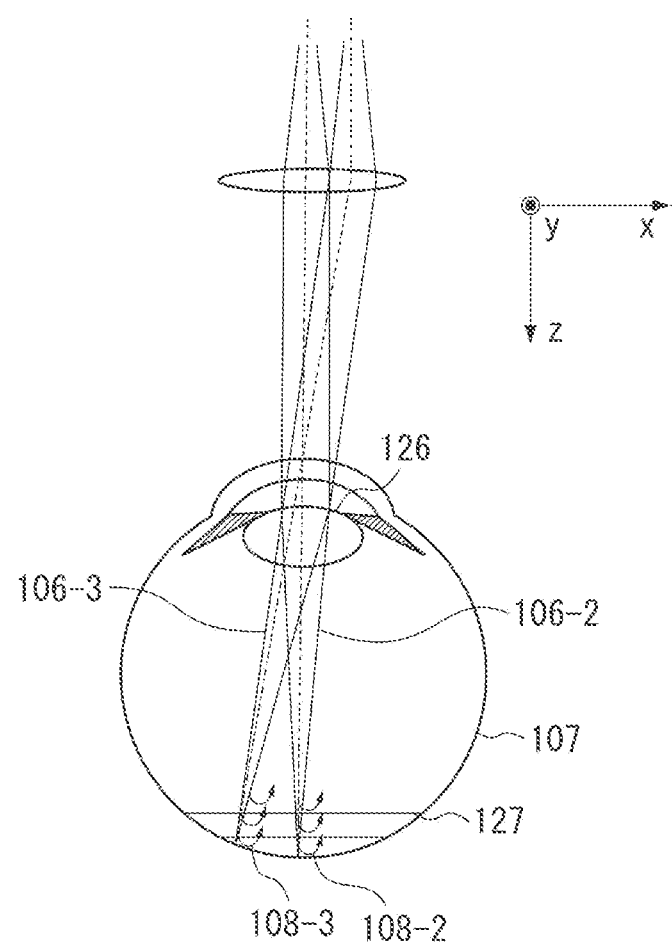
FIG. 2A is a schematic diagram illustrating acquisition of a tomographic image by the ophthalmologic apparatus.

FIG. 2A illustrates the test eye 107 which is observed by the OCT apparatus 100. In FIG. 2A, the measurement light beam 106-1 is omitted. Units that are identical to or correspond to those illustrated in FIG. 1 are denoted with the same reference numerals, and a description of the overlapping units will be omitted.

As illustrated in FIG. 2A, when the measurement light beams 106-2 and 106-3 pass through the iris 126 and are incident on the fundus 127, these measurement light beams 106-2 and 106-3 turn into the returning light beams 108-2 and 108-3 due to reflection and scattering at various positions, and arrive at the line sensor 139 with a time delay at each of those positions. Although the returning light beams 108-2 and 108-3 are illustrated in FIG. 2A without an axis for ease of understanding, in actual fact the returning light beams 108-1 to 108-3 are returning light that tracks back along the path of the measurement light beams 106-1 to 106-3 in reverse.

Figure 2B:
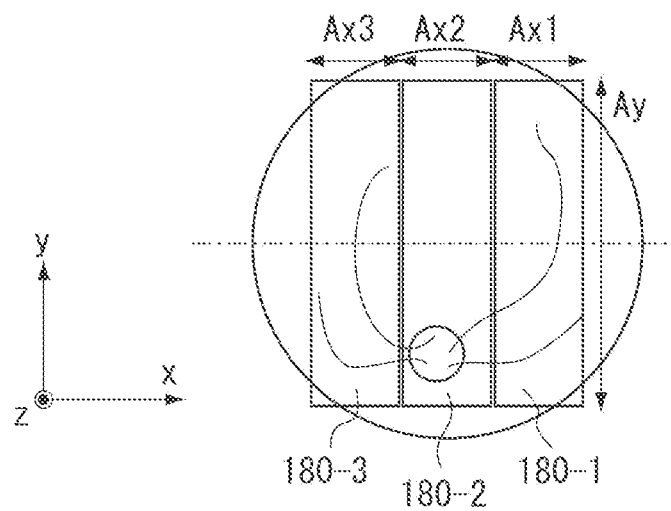
FIG. 2B is a schematic diagram illustrating acquisition of a tomographic image by the ophthalmologic apparatus.

FIG. 2B illustrates which region on the fundus each of the measurement light beams 106-1 to 106-3 observes. The measurement light beams 106-1 to 106-3 are used to scan regions 180-1 to 180-3 respectively to observe each region. If respective scan angles in an initial state are expressed as a beam shift angle scanning near the iris 126, the scan angle corresponding to a scanning width Ay is ±18° to the optical axis center for each of the measurement light beams in the y direction, and the scan angle of the scanning widths Ax1 to Ax3 is 12° for each of the measurement light beams.

The scanning width Ay can be changed by the shift width of the mirror scanning the Y axis side of the XY scanner. Further, an interval between the scanning widths Ax1 to Ax3 (12° in the initial state) can be changed by movement of the fiber end which is described below. The "initial value" is a wide viewing angle mode for observing the fundus at a wide angle of view.

Since the band width of the light source 101 is wide and a spatial coherence length is short, an interference fringe can be detected by the line sensor 139 only when the light path length of the reference light paths and the light path length of the measurement light paths are roughly equal. As described above, an interference fringe in the spectral region on the wavelength axis is acquired by the line sensor 139.

Next, the interference fringes which are information about the wavelength axis are converted into an interference fringes of an optical frequency axis for each of the multiplexed light beams 142-1 to 142-3, taking into consideration the properties of the line sensor 139 and the transmissive diffraction lattice 141. In addition, information about the depth direction can be obtained by subjecting the converted optical frequency axis interference fringes to Fourier transform.

While driving the mirror on the Y axis side of the XY scanner 119, if an interference fringe is detected, an interference fringe can be obtained at each position on the Y axis. More specifically, information about the depth direction can be obtained for each position on the Y axis.

Figure 2C:
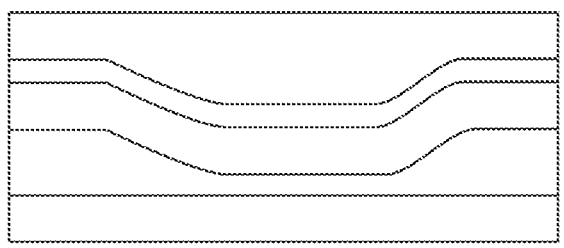
FIG. 2C is a schematic diagram illustrating acquisition of a tomographic image by the ophthalmologic apparatus.
Figure 2C:
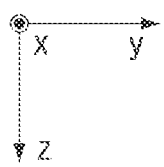

Consequently, a two-dimensional distribution of the intensity of the returning light beam 108-1 on the yz plane can be obtained. The obtained two-dimensional distribution is, specifically, a tomographic image 132 (FIG. 2C). The tomographic image 132 is based on the intensity of the returning light beam 108-1 in an array pattern. For example, the tomographic image 132 is displayed by applying the intensity to a grey scale. FIG. 2C is illustrated with only boundaries of the obtained tomographic image highlighted.

Figure 2D:
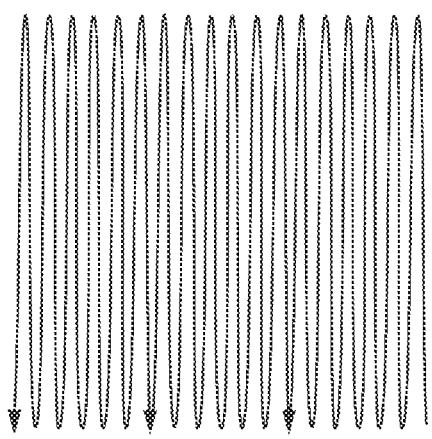
FIG. 2D is a schematic diagram illustrating acquisition of a tomographic image by the ophthalmologic apparatus.
Figure 2D:
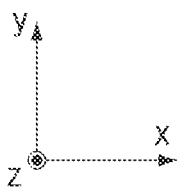

Further, as illustrated in FIG. 2D, if the measurement light beams 106-1 to 106-3 are each raster-scanned over the fundus by controlling the XY scanner 119, tomographic images of arbitrary locations on the fundus can be consecutively and simultaneously acquired. FIG. 2D illustrates scanning performed when a main scanning direction of the XY scanner is set as the Y axis direction and a sub-scanning direction is set as the X axis direction, which consequently allows a plurality of tomographic images in the yz plane to be obtained.

A Mach-Zehnder interferometer may also be used as the interferometer. If using a Mach-Zehnder interferometer, although the configuration is more complex than a Michelson interferometer, there is an advantage that when the ratio between measurement light and reference light is smaller, the obtained tomographic images have a high contrast.

Figure 3A:
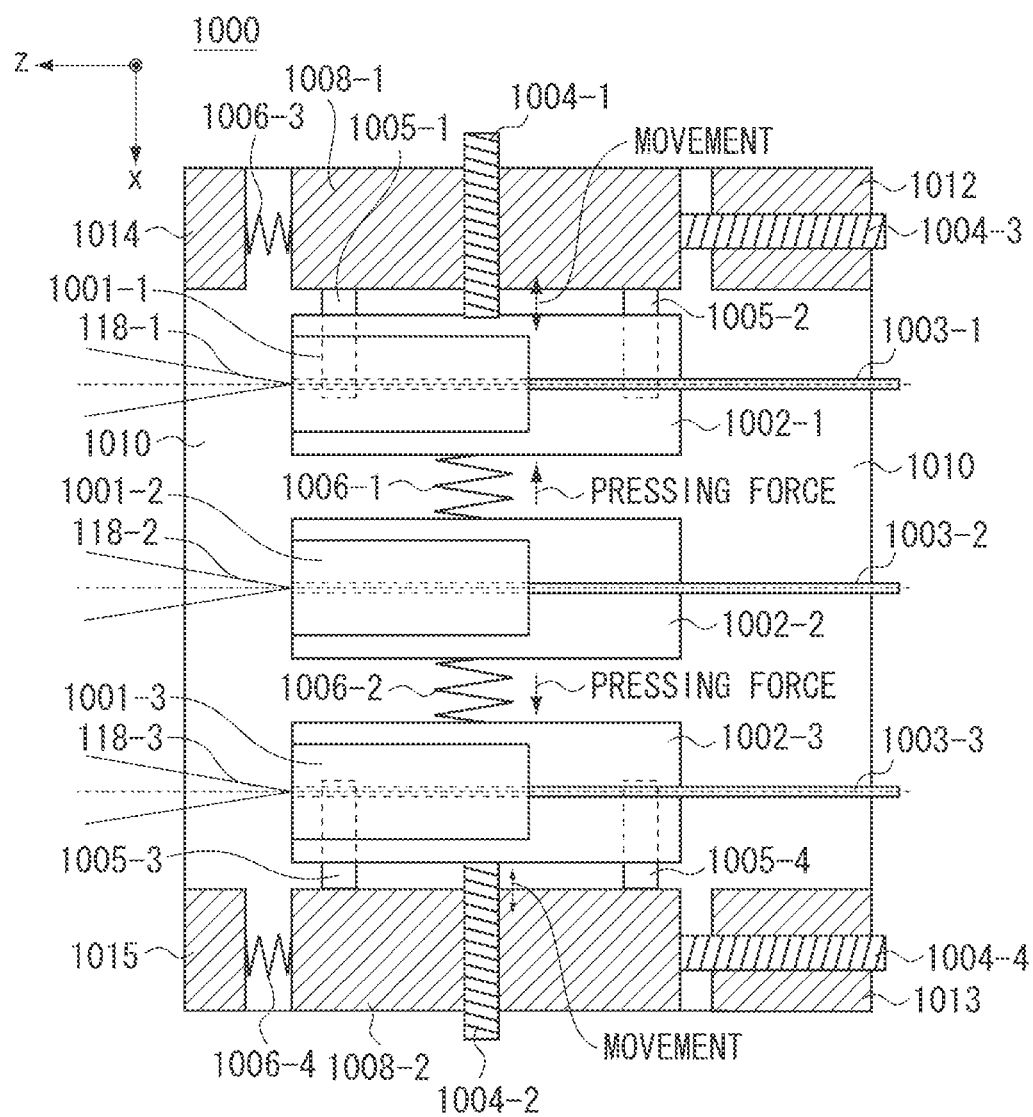
FIG. 3A is a schematic diagram illustrating a configuration of a fiber end adjustment mechanism in the ophthalmologic apparatus.

A fiber end adjustment mechanism will now be described with reference to FIGS. 3A and 3B. FIG. 3A is a view of a fiber unit as seen from the y direction, and FIG. 3B is a view as seen from the x direction.

Figure 3B:
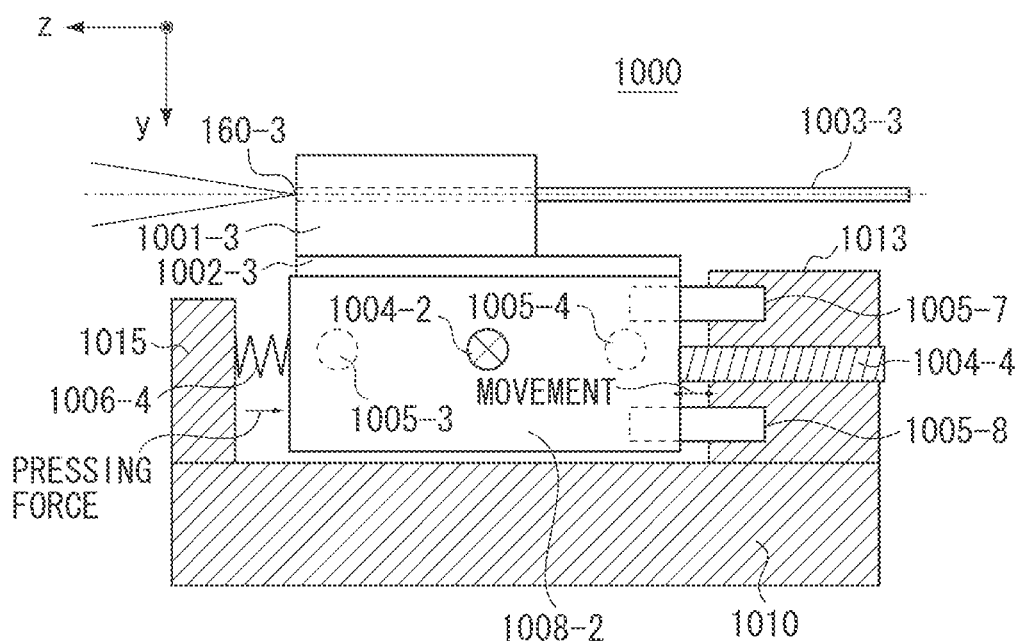
FIG. 3B is a schematic diagram illustrating a configuration of a fiber end adjustment mechanism in the ophthalmologic apparatus.

The fiber end adjustment mechanism illustrated in FIGS. 3A and 3B includes a fiber unit 1000 and fiber portions 1003-1 to 1003-3 which are respectively connected to the measurement light side of the optical couplers 131-1 to 131-3. The fiber portions 1003-1 to 1003-3 are respectively fixed to holding portions 1001-1 to 1001-3 which are formed by sandwiching the fibers with a material such as quartz, and polishing the fiber ends 118-1 to 118-3 side. Further, the holding portions 1001-1 to 1001-3 are bonded and fixed to fiber base portions 1002-1 to 1002-3, respectively.

The center fiber base portion 1002-2 is fixed to a base 1010 by a not-illustrated screw, for example. By adjusting the base 1010 in the optical axis position (x, y) and the optical axis direction (z) in FIG. 1, the center fiber end 118-2 can be aligned with the optical axis of the apparatus, and be optimally positioned at which the measurement light 160-2 can be the parallel light by the collimator lens 130-2.

The upper and lower fiber base portions 1002-1 and 1002-3 in FIG. 3A can be relatively moved with respect to the center fiber base portion 1002-2 in a fiber interval direction (x direction). Taking the upper fiber base portion 1002-1 as an example, the fiber base portion 1002-1 includes guide portions into which pins 1005-1 and 1005-2 are inserted. The pins 1005-1 and 1005-2 are fixed to an X guide member 1008-1. The upper fiber base portion 1002-1 is held by these pins 1005-1 and 1005-2 so that it can move in the x direction.

Further, a spring 1006-1 is provided between the fiber base portions 1002-1 and 1002-2. Consequently, the fiber base portion 1002-1 is pressed toward an arrow (pressing) direction in the y direction. A screw hole is provided in the X guide member 1008-1, into which an adjustment screw 1004-1 is inserted. The adjustment screw 1004-1 abuts on the fiber base portion 1002-1 to position the fiber base portion 1002-1 in the y direction.

By rotating the adjustment screw 1004-1, the interval between the fiber base portions 1002-1 and 1002-2 can be varied in the arrow (movement) direction. Accordingly, the interval between the fiber ends 118-1 and 118-2 can be adjusted. A similar configuration may be also provided on the fiber base portion 1002-3 side, so that the interval between the fiber ends 118-2 and 118-3 can be adjusted. Consequently, the relative interval among the measurement light beams 106-1 to 106-3 can be adjusted, enabling the initial state to be adjusted to 12° on the fundus.

The upper and lower X guide members 1008-1 and 1008-2 in FIG. 3A can be relatively moved with respect to the center fiber base portion 1002-2 in the optical axis direction (z direction). The X guide member 1008-2 will now be described as an example with reference to FIGS. 3A and 3B. Pins 1005-7 and 1005-8 are fixed to a z guide portion 1013 which is integrated with the base 1010. The X guide member 1008-2 includes guide portions into which the pins 1005-7 and 1005-8 are inserted. These pins 1005-7 and 1005-8 hold the X guide member 1008-2 so that it can move in the z direction. Further, a spring 1006-1 is provided between the X guide member 1008-2 and a member 1015 which is integrated with the base 1010. Consequently, the X guide member 1008-2 is pressed toward the arrow (pressing) direction in the z direction.

A screw hole is provided in the z guide portion 1013, into which an adjustment screw 1004-4 is inserted. The adjustment screw 1004-4 abuts on the X guide member 1008-2 to position the X guide member 1008-2 in the z direction. By rotating the adjustment screw 1004-4, the X guide member 1008-2 can be moved in the arrow (movement) direction. Accordingly, the relative position in the z direction between the fiber ends 118-1 and 118-2 can be adjusted.

A similar configuration is also provided on the fiber end 118-1 side. The relative positions of the fiber ends 118-1 to 118-3 are adjusted based on their initial state so that the focal position matches a fundus shape of a standard test eye.

Figure 4A:
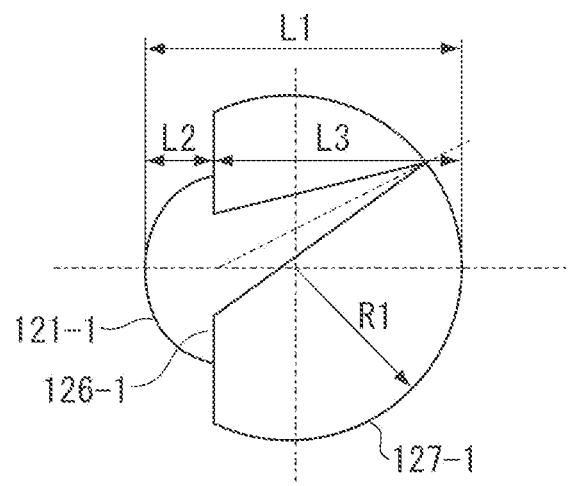
FIG. 4A illustrates focal position deviation of a fundus in the ophthalmologic apparatus.

The fundus of the standard test eye will now be schematically described with reference to FIG. 4A. FIG. 4A is a schematic diagram illustrating a cornea 121-1, an iris 126-1, and a fundus 127-1 that is assumed to have a spherical shape. A distance (eye axial length) L1 between an apex on the optical axis of the cornea 121-1 and the fundus 127-1 is 23 mm. A distance L2 between the apex on the optical axis of the cornea 121-1 and the iris 126-1 is 3.5 mm. A radius of curvature R1 of the fundus 127-1 is 12 mm. A distance L3 from the iris 126-1 to the fundus 127-1 is 19.5 mm.

Figure 4B:
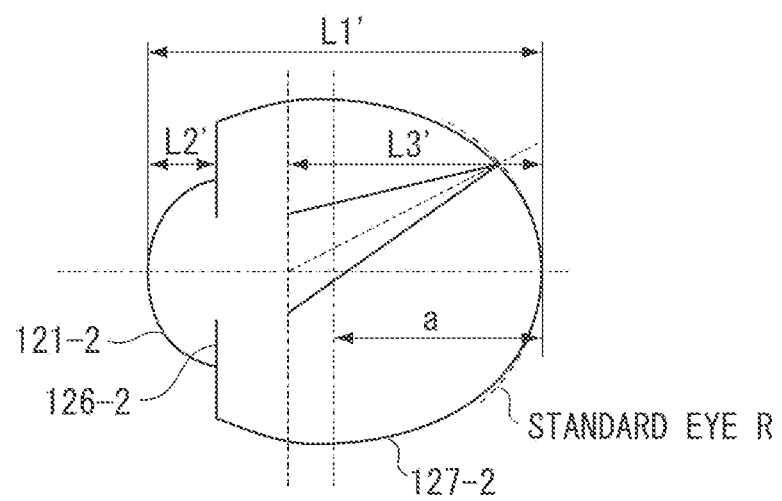
FIG. 4B illustrates focal position deviation of a fundus in the ophthalmologic apparatus.

The shape of the test eye when the eye axial length is long will now be schematically described with reference to FIG. 4B. In this case, a cross-sectional shape of the fundus is approximate to an ellipse. FIG. 4B is a schematic diagram illustrating a cornea 121-2, an iris 126-2, and a fundus 127-2. A distance (eye axial length) L1' between an apex on the optical axis of the cornea 121-2 and the fundus 127-2 is 30 mm. A distance L2' between the apex on the optical axis of the cornea 121-2 and the iris 126-2 is 3.5 mm. A long axis side radius a of the fundus 127-2 is 16 mm.

When a tomographic image of the fundus of the standard test eye is captured, an image plane of each measurement light beam on the fundus 127-1 is brought into focus by moving the lens 120-2 with respect to the fundus 127-1 in the z axis direction using the electric stage 172-2. Consequently, even if a depth of focus of each measurement light beam is narrow, the focal positions are in focus, so that the tomographic image in good condition can be acquired. On the other hand, in the case of the above described test eye with the long eye axial length, the image plane can be adjusted to a position on the optical axis of the fundus 127-2 by moving the lens 120-2 in the z axis direction. However, at positions on the fundus where the scan angle of the beam is large, a deviation occurs between the image plane and the fundus.

Figure 4C:
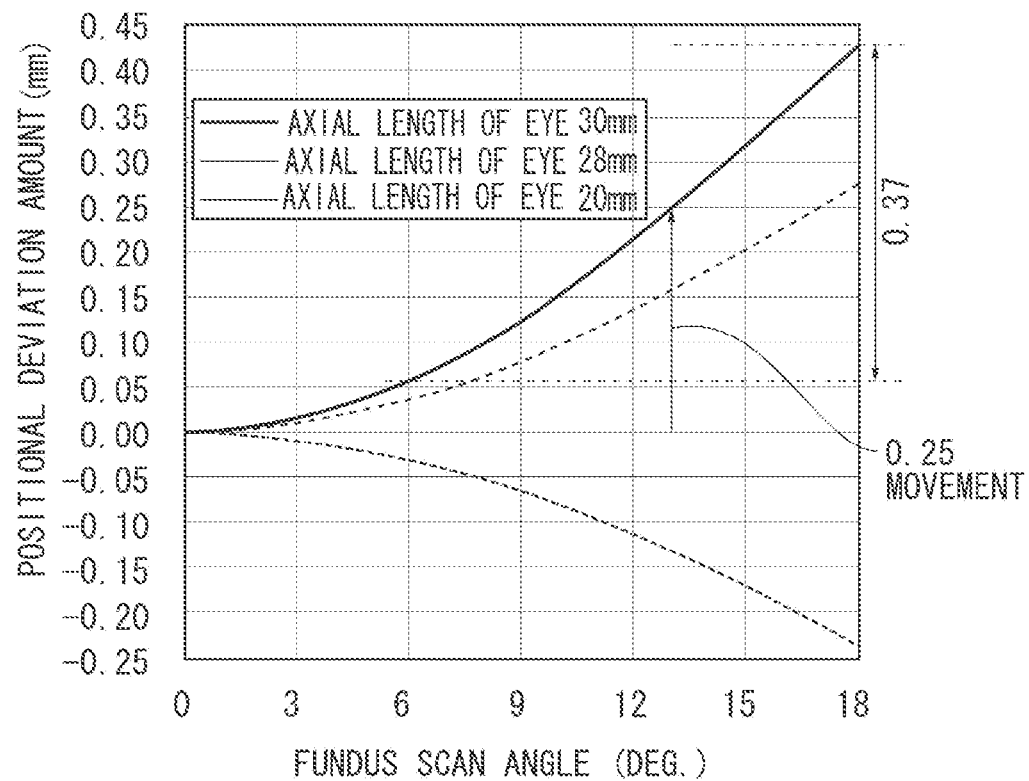
FIG. 4C illustrates focal position deviation of a fundus in the ophthalmologic apparatus.

Such case will be illustrated in FIG. 4C. In FIG. 4C, the horizontal axis represents the scan angle with the optical axis being 0°, and the vertical axis represents a difference (fundus positional deviation amount) in the fundus position between the standard test eye and the test eye for each eye axial length. In FIG. 4B, this corresponds to a distance at each angle of view between the fundus 127-2 and the fundus of the standard eye represented by the dotted line. This distance is a result calculated by approximating the cross-sectional shape of each test eye (other than the standard test eye) to an ellipse. For example, if the eye axial length in the above numerical example is 30 mm, the fundus positional deviation amount at the edge sides in the wide angle mode (18°) is more than 0.4 mm. A similar example will be shown for each eye axial length.

On the other hand, depending on the depth of focus of the measurement light, the fundus positional deviation amount can exceed the depth of focus, which can cause the tomographic image resolution to deteriorate.

The depth of focus (DOF) of an imaging system is represented by the following equation (1),

[Math. 1]

$$DOF = \pm k_2 * (\lambda/NA^2) \quad (1)$$

in which $k_2$ is a constant of about 0.6.

In the above equation (1), DOF is the depth of focus, NA represents numerical apertures of an eye forming an image from parallel measurement light, and λ represents the center wavelength of the measurement light. NA is determined based on the light beam diameter and the focal distance of the eye. When the focal distance of the eye is 22.5 mm, $NA \approx d/(2*f)$ (wherein d represents the light beam diameter on the iris 126, and f represents the focal distance of the eye during measurement).

In the present exemplary embodiment, the light beam diameter is 2.2 mm. Thus, using $NA_{d-2.2mm} = 0.049$ into the above calculation, DOF can be calculated as ±0.2 mm.

When the fundus in FIG. 4C having an eye axial length of 30 mm is measured with this DOF value, although the center beam (observation at a ±6° angle of view) is within the DOF range, at the maximum angle of view 18° position for the beams on the edge sides, the beams miss the DOF range.

Accordingly, the DOF range of each measurement light beam can be positioned on the fundus even for this eye axial length by moving each of the fiber ends 118-1 and 118-3 on the edge sides in the z direction. More specifically, it is most desirable that the DOF center position is located in the middle of the fundus difference. The measurement light beams on the edge sides are used for scanning over a scan angle range of 6° to 18°. Further, there is a difference in the fundus positional deviation amount of 0.37 mm between these scan angles. Therefore, the image plane of the beams on the edge sides is moved about (0.6+0.37/2)=0.25 mm (see an arrow in FIG. 4C). If the movement is converted into a fiber end movement amount, based on a vertical magnification of the optical system from the fiber ends 118-1 to 118-3 to the fundus 127 of 25, the fiber ends are moved by 0.01 mm in the z direction which is an arrow (minus) direction in FIG. 3A.

Thus, the fundus positional deviation amount can be estimated from the eye axial length. Based on the estimated amount, a movement amount in the fiber optical axis direction can be calculated. Further, by moving the fiber ends, which are the output ends of the measurement light, based on the movement amount, the fundus can be kept within the DOF, so that a tomographic image can be obtained in which the resolution does not change from the center beam.

For the examples of other eye axial lengths illustrated in FIG. 4C (28 mm and 20 mm), since both of these cases have an angle of view that is up to 18°, which is within the DOF, if the light beam diameter is 2.2 mm, the fiber ends on the edges do not have to be moved.

If the DOF changes from that described above, more specifically, if the beam diameter on the iris 126 is changed by the above-described beam expander, a determination is made regarding whether to move the fiber ends on the edge sides by comparing the DOF value and the fundus positional deviation amount.

Further, in some cases the regions scanned by the respective measurement light beams are changed. For example, a case will be considered in which the scanning regions Ax1 to Ax3 in FIG. 2B are reduced in size. Such case is performed when scanning a region which a user wishes to pay particular attention to at a high density. In such a case, the scanning is performed by moving the fiber ends 118-1 and 118-3 in the x direction. If the scanning regions Ax1 to Ax3 are respectively scanned at a scan angle of 6°, the overall scan angle in the x direction is 18° (the fiber ends 118-1 and 118-3 are closer to the fiber end 118-2 than in the wide angle mode). In FIG. 4C, if the eye axial length is 30 mm at a scan angle of 9° on one side, the fundus positional deviation amount is 0.124 mm. Consequently, when the light beam diameter is 2.2 mm, the fundus is sufficiently within the DOF, so that there is no need to move the fiber ends. Obviously, it may be necessary to move the fiber ends if the DOF is narrowed due to changes in the light beam diameter.

Figure 5A:
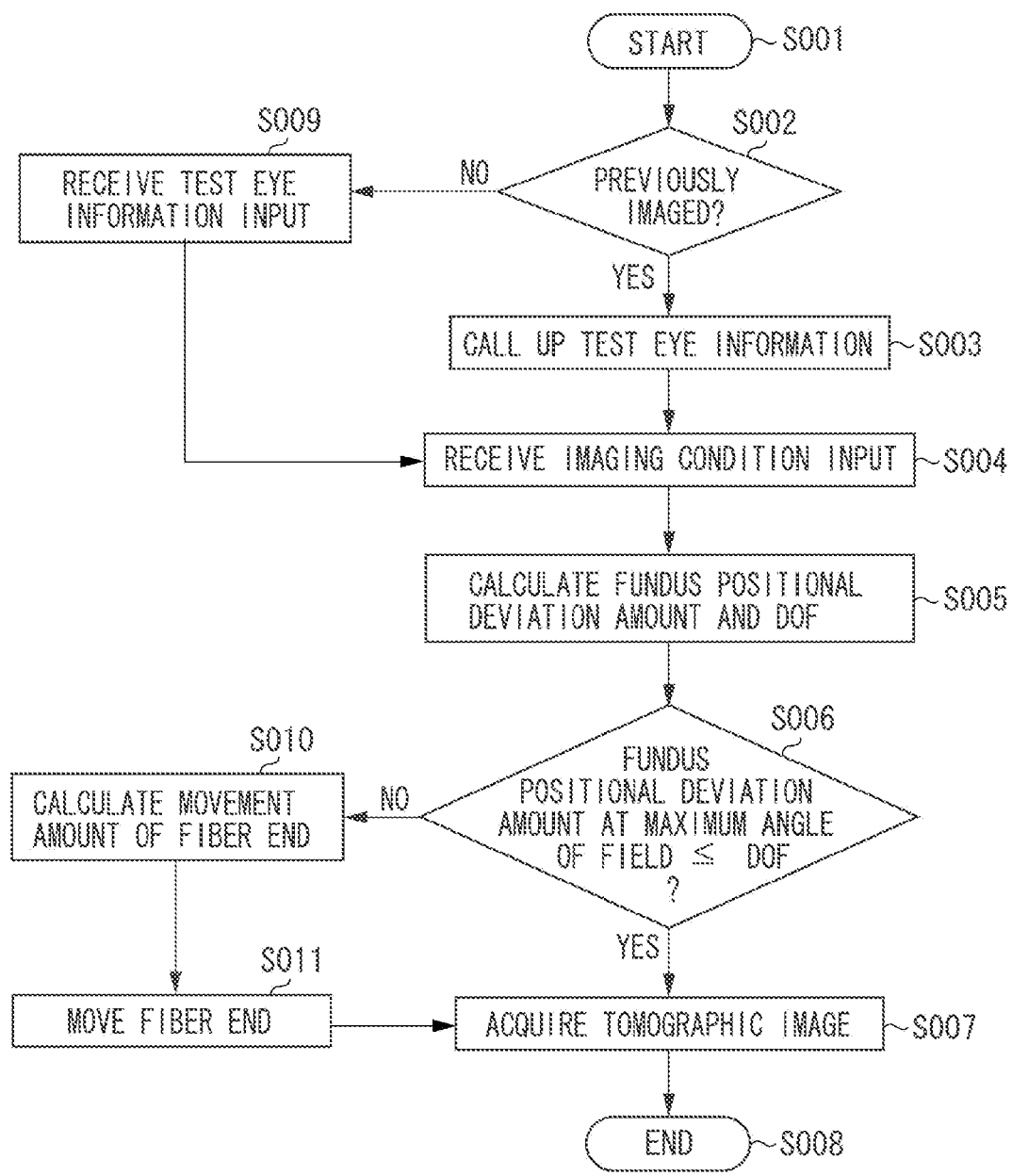
FIG. 5A is a flowchart illustrating focal position adjustment in the ophthalmologic apparatus.

The flow of capturing a tomographic image in which the light beam diameters and the scanning regions can be changed will be described step by step with reference to FIG. 5A.

In step S001, imaging starts under the control of the control unit (CPU) 125. Then, the processing proceeds to step S002.

In step S002, an input regarding whether the test eye is an eye which an operator has imaged in the past is received from the operator. The processing in step S002 may also be performed by displaying on a display unit information about test eyes that were imaged in the past so that the operator can select a target test eye from among them. If it is determined that the test eye is a previously-imaged eye (YES in step S002), the processing proceeds to step S003. If it is determined that the test eye is not a previously-imaged eye (NO in step S002), the processing proceeds to step S009.

In step S003, test eye information is called up from past imaging data under the control of the control unit (CPU) 125. In step S003, an acquisition unit 500 (not illustrated) acquires information relating to the shape of the test eye. For example, such information includes an eye axial length, right and left of the test eye, and refractive power. The information may further include a patient identification (ID), name, date of birth, and sex for acquiring the shape of the test eye. If the test eye information is changed from the past imaging data, the test eye information is edited and rewritten. Then, the processing proceeds to step S004.

In step S009, input of the test eye information is received. Then, the processing proceeds to step S004.

In step S004, the acquisition unit 500 receives an imaging condition input. The imaging conditions may include a region in which a tomographic image is captured (from which the maximum angle of view in the x direction are guided), the number of scanning locations included in one scanning in the yz plane in FIG. 2D (corresponding to a tomographic image density), and the light beam diameter on the iris. Then, the processing proceeds to step S005.

In step S005, a calculation unit 510 (not illustrated) calculates the maximum fundus positional deviation amount based on the input eye axial length and the maximum angle of view in the x direction used in imaging, and the DOF in this imaging based on the light beam diameter on the iris. Then, the processing proceeds to step S006.

In step S006, the calculation unit 510 compares the maximum fundus positional deviation amount with the DOF value. If the maximum fundus positional deviation amount is equal to or less than the DOF (YES in step S007), the processing proceeds to step S007. If the maximum fundus positional deviation amount is greater than the DOF (NO in step S007), the processing proceeds to step S010.

In step S010, the calculation unit 510 calculates a fiber end movement amount on the edge sides. According to the example described above, the fiber end movement amount is 0.01 mm. Then, the processing proceeds to step S011.

In step S011, the fiber ends on the edge sides are moved under the control of the control unit (CPU) 125 by the fiber end movement amount only. Then, the processing proceeds to step S007.

If the eye axial length is within a predetermined range of a standard eye axial length, only the electric stage 120-2 is moved with the position of the fiber ends as an initial value.

In step S007, a tomographic image is acquired by scanning the fundus by each of the measurement light beams according to the imaging conditions under the control of the control unit (CPU) 125. The processing in step S007 also includes confirmation and display of the tomographic image. Then, the processing proceeds to step S008. If the eye axial length is within the predetermined range of the standard eye axial length (for example, between 28 mm to 20 mm), only the electric stage 120-2 is moved with the position of the fiber ends as an initial value. Then, in step S008, imaging is finished.

The order of processing illustrated in the flowchart may be appropriately changed within a feasible range. For example, the input of the imaging conditions performed in step S004 may be performed immediately after imaging is started in step S001.

As described above, in the present exemplary embodiment, the depth of each measurement light beam can be positioned on the fundus position by moving a relative position in the optical axis direction (z direction) of each fiber end based on the eye axial length, that is information about the test eye, and information about the imaging conditions (the light beam diameter on the iris and the scanning region). Consequently, a good tomographic image can be acquired.

Although in the present exemplary embodiment, an OCT apparatus that acquires a tomographic image of a fundus is described, the same effects can be obtained even if a scanning laser ophthalmoscope (SLO) is employed.

Further, the present invention is not limited to the fundus, and may be applied to an anterior eye. In this case, a surface image is acquired rather than a tomographic image. In addition, although in the above described exemplary embodiment, the x direction range of the scanning region is adjusted by the fiber ends, the present invention is not limited to this configuration. For example, a zoom function may be included in the optical system between the fiber ends 118-1 and 118-3 and the test eye 107.

Like the first exemplary embodiment, an ophthalmologic apparatus according to a second exemplary embodiment is an OCT apparatus which acquires a tomographic image of a fundus. The difference from the first exemplary embodiment is how the movement amount of the fiber ends is determined. Therefore, a description of the parts that are common in the first and second embodiments will be omitted. In the present exemplary embodiment, the fiber ends are moved based on a tomographic image.

One example is to cause an operator to move a depth position of each measurement light beam while the apparatus displays a tomographic image.

Figure 6:
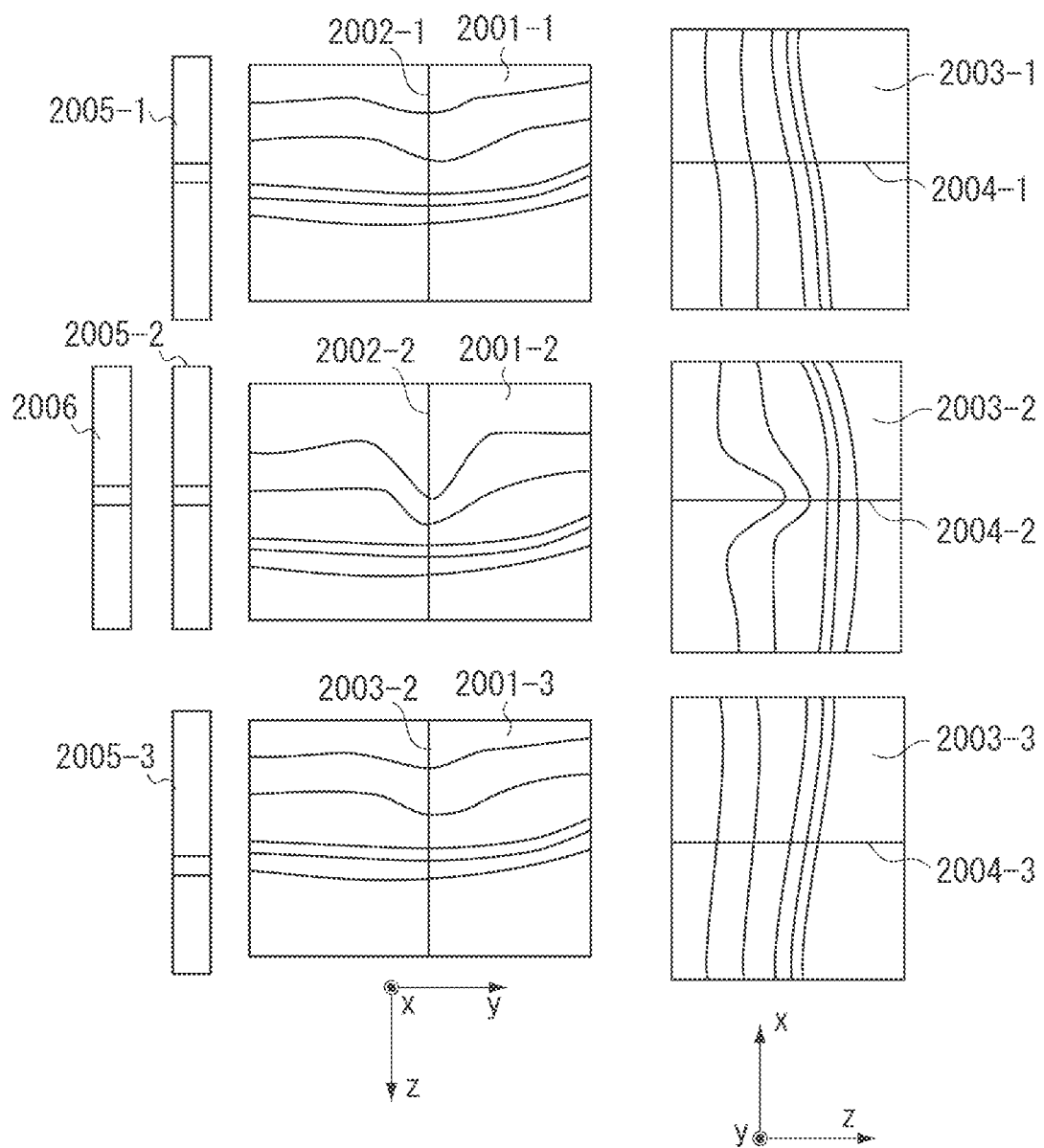
FIG. 6 illustrates a display screen displayed by the ophthalmologic apparatus.

FIG. 6 illustrates a tomographic image adjustment screen. The adjustment screen displays an image output under the control of the control unit (CPU) 125 on a monitor (not illustrated in FIG. 1). In FIG. 6, tomographic images 2001-1 to 2001-3 are tomographic images in the yz direction of the fundus 127 produced by the measurement light beams 106-1 to 106-3, respectively, and tomographic images 2003-1 to 2003-3 are tomographic images in the xz direction. Further, the tomographic images 2001-1 to 2001-3 are tomographic images of near indicator lines 2004-1 to 2004-3 in the tomographic images 2003-1 to 2003-3, respectively. The tomographic images 2003-1 to 2003-3 are tomographic images of near indicator lines 2002-1 to 2002-3 in the tomographic images 2001-1 to 2001-3, respectively. The respective tomographic images in the adjustment screen have a lower scanning density than the images that are actually acquired and stored, so that display update can be performed quickly.

A gate adjustment slider 2006 enables the electric stage 117-1 illustrated in FIG. 1 to be moved based on an operation of the gate adjustment slider 2006. While looking at the respective tomographic images, the operator performs adjustment by operating the gate adjustment slider 2006 so that the respective tomographic images are displayed within the display screen without disruption.

A focus adjustment slider 2005-2 enables the electric stage 117-2 illustrated in FIG. 1 to be moved based on an operation of the focus adjustment slider 2005-2. While looking at a target layer in cross-sections in the tomographic images 2001-2 and 2003-2, the operator performs adjustment by operating the focus adjustment slider 2005-2 so that the target layer in the cross-sections has the highest luminance.

Further, focus adjustment sliders 2005-1 and 2005-3 enable a motor (not illustrated) to rotate. The motor is mechanically connected so that both of the adjustment screws 1004-3 and 1004-4 illustrated in FIGS. 3A and 3B can rotate based on an operation of the focus adjustment sliders 2005-1 and 2005-3. While looking at a target layer in the cross-sections of the tomographic images 2001-1 and 2003-1, the operator performs adjustment by operating the focus adjustment slider 2005-1 so that the target layer has the highest luminance. Further, while looking at the target layer in the cross-sections of the tomographic images 2001-3 and 2003-3, the operator performs adjustment by operating the focus adjustment slider 2005-3 so that the target layer in the cross-sections has the highest luminance.

Consequently, unlike the first exemplary embodiment, the fiber ends on the edges can be adjusted while directly looking at the fundus state of the test eye without having to assume that the fundus has a round or elliptical cross-section. Therefore, the fundus can be imaged within the DOF even for various types of test eyes whose fundus has a shape that is not a round or elliptical cross-section. Although each of these sliders is described as being operated by displaying on a screen, the sliders may also be operated by a joystick or a mouse connected to a control unit 200.

Figure 5B:
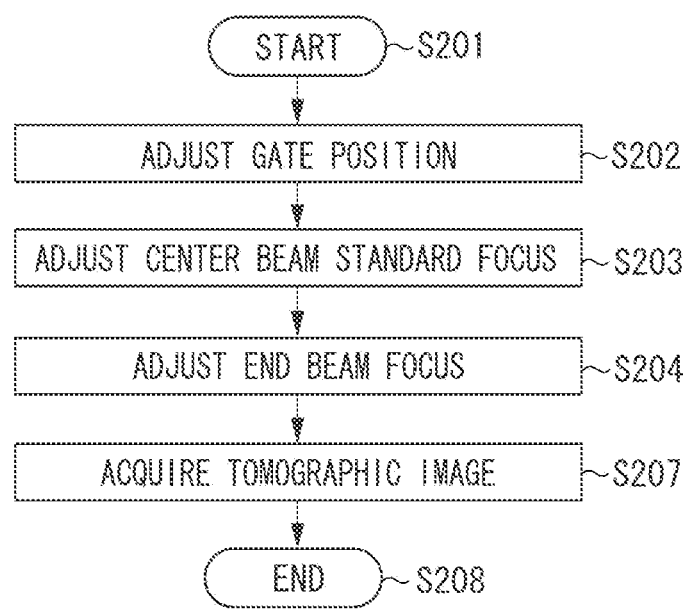
FIG. 5B is a flowchart illustrating focal position adjustment in the ophthalmologic apparatus.

As a modification of the above described exemplary embodiment, the fiber ends may be automatically adjusted based on the target layer in the tomographic images, or the luminance of the overall fundus cross-section, or the contrast with the background as an index. A processing flow for acquiring a tomographic image by automatically performing gate position adjustment, overall focus adjustment, and individual fiber position adjustment will now be described with reference to FIG. 5B.

In step S201, imaging starts under the control of the control unit (CPU) 125. Then, the processing proceeds to step S202.

In step S202, gate position adjustment is performed. The calculation unit 510 acquires a tomographic image to be used for adjustment from the center measurement light beam 106-2, extracts high luminance points from the whole fundus image, and calculates a luminance ratio with a background portion for which there is no tomographic image. Further, while moving the electric stage 117-1 under the control of the control unit 200, the electric stage 117-1 is stopped at a position where the luminance ratio is the highest. Then, the processing proceeds to step S203.

In step S203, focus adjustment is performed with the center measurement light beam 106-2 as a reference under the control of the control unit (CPU) 125. The calculation unit 510 acquires a tomographic image to be used for adjustment from the center measurement light beam 106-2, and calculates an average luminance of a target layer in the cross-sections. Further, while moving the electric stage 117-2 under the control of the control unit 200, the electric stage 117-2 is stopped at a position where the luminance is the highest. Then, the processing proceeds to step S204.

In step S204, the control unit 200 performs focus adjustment of the measurement light beams 106-1 and 106-3 on the edge sides. Taking the measurement light beam 106-1 as an example, the calculation unit 510 acquires a tomographic image to be used for adjustment from the measurement light beam 106-1, and calculates an average luminance of the target layer in the cross-sections. The control unit 200 rotates a motor (not illustrated) that is mechanically connected to the adjustment screw 1004-3, so that the electric stage 117-2 is stopped at a position where the luminance is the highest. Then, the processing proceeds to step S207.

In step S207, a tomographic image is acquired. Then, the processing proceeds to step S208, and imaging is finished.

The target layer is often different based on a lesion which the operator wishes to observe. For glaucoma, the target layer is usually a layer near the fundus surface. For macular disease, the target layer is usually a pigment epithelial layer positioned on the lower side of the cross-section. To calculate the average luminance of the target layer, a known segmentation method may be employed.

Further, although the above processing flow uses the average luminance of the target layer as an index for focus adjustment, the total luminance of all the cross sections, or a luminance ratio like that used as an index for gate adjustment may also be used as the index. In addition, similar to the first exemplary embodiment, the present exemplary embodiment may also be applied in an SLO.

Thus, in the ophthalmologic apparatus according to the present exemplary embodiment, the quality of an image acquired based on respective measurement light beams by performing focus position adjustment on a plurality of beams when the focal positions are different at the center and the periphery can be improved for an even wider range of test eye shapes than in the first exemplary embodiment.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent No. 2010-082805, filed Mar. 31, 2010, which is hereby incorporated by reference herein in its entirety.

The invention claimed is:
1. An ophthalmologic apparatus, comprising:
a scanning optical system configured to scan a plurality of different regions of a test eye with a plurality of different measurement light beams;
an acquisition unit configured to acquire information about a shape of the test eye; and an adjustment unit configured to adjust a relative position between an output end of a measurement light beam that serves as a reference among the plurality of measurement light beams and an output end of other measurement light beams among the measurement light beams based on the acquired information about the shape of the test eye.

2. The ophthalmologic apparatus according to claim 1, further comprising:

an electric stage configured to simultaneously change a plurality of focal positions of measurement light beams output from the adjustment unit, wherein the information about the shape of the test eye is an eye axial length, and wherein, if the eye axial length is within a predetermined range from a standard eye axial length, only the electric stage is moved with a position of the adjustment unit as an initial value.

3. The ophthalmologic apparatus according to claim 1, wherein the adjustment unit changes an interval between the measurement light beams on the fundus by adjusting the relative position between the output end of the measurement light beam that serves as the reference and the output end of other measurement light beams.

4. The ophthalmologic apparatus according to claimed 1, further comprising a unit configured to change a diameter of a light beam that is incident on the test eye among the plurality of measurement light beams.

5. The ophthalmologic apparatus according to claim 1, wherein the information about the test eye is an eye axial length.

6. The ophthalmologic apparatus according to claim 1, further comprising a calculation unit configured to calculate a movement amount of the relative position based on an image obtained from the fundus of the test eye.

7. A method for controlling an ophthalmologic apparatus which includes a scanning optical system configured to scan different regions on a fundus of a test eye with a plurality of measurement light beams, the method comprising:

acquiring information about a shape of the test eye; and adjusting a relative position between an output end of a measurement light beam that serves as a reference among the plurality of measurement light beams and an output end of other measurement light beams among the measurement light beams based on the acquired information about the shape of the test eye.

* * * * *